US009482649B2

(12) United States Patent
Lueth et al.

(10) Patent No.: US 9,482,649 B2
(45) Date of Patent: Nov. 1, 2016

(54) FITTING FOR ELASTICALLY-BIASING A CAPILLARY FOR A FLUID-TIGHT CONNECTION TO A FLUIDIC CONDUIT

(71) Applicant: AGILENT TECHNOLOGIES, INC., Loveland, CO (US)

(72) Inventors: Claus Lueth, Waldbronn (DE); Darijo Zeko, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/394,590

(22) PCT Filed: Nov. 15, 2012

(86) PCT No.: PCT/IB2012/056463
§ 371 (c)(1),
(2) Date: Oct. 15, 2014

(87) PCT Pub. No.: WO2014/076522
PCT Pub. Date: May 22, 2014

(65) Prior Publication Data
US 2015/0090595 A1    Apr. 2, 2015

(51) Int. Cl.
*G01N 30/60*    (2006.01)
*B01D 15/22*    (2006.01)
*B01D 53/04*    (2006.01)
*B01D 57/02*    (2006.01)
(Continued)

(52) U.S. Cl.
CPC ............... *G01N 30/60* (2013.01); *B01D 15/22* (2013.01); *B01D 53/0407* (2013.01); *B01D 57/02* (2013.01); *F16L 15/08* (2013.01); *F16L 19/02* (2013.01); *G01N 30/6026* (2013.01); *G01N 2030/025* (2013.01); *G01N 2030/027* (2013.01); *Y10T 29/49826* (2015.01)

(58) Field of Classification Search
None
See application file for complete search history.

(56) References Cited

U.S. PATENT DOCUMENTS

| 4,991,883 A | 2/1991 | Worden |
| 5,234,235 A | 8/1993 | Worden |

(Continued)

FOREIGN PATENT DOCUMENTS

| GB | 2482175 A | 1/2012 |
| WO | WO2011076244 | 6/2011 |

OTHER PUBLICATIONS

International Search Report & Written Opinion mailed Aug. 12, 2013 for International Application No. PCT/IB2012/056463.
(Continued)

*Primary Examiner* — Jill Warden
*Assistant Examiner* — Matthew Krcha

(57) ABSTRACT

A fitting (200) for providing a fluid connection between a capillary (202) and a fluidic conduit (204) of a fluidic component (30), the fitting (200) comprising a male piece (240) and a female piece (250) for connection with the male piece (240), wherein the male piece (240) comprises a housing (252) with a capillary reception (212) configured for receiving the capillary (202), wherein a part of the capillary (202) being received in the capillary reception (212) is circumferentially covered by a sleeve (214), an elastic biasing mechanism (206) being arranged at least partially within the housing (252), being configured for biasing the capillary (202) against the female piece (250) and being supported by the sleeve (214), and a locking mechanism (208) being arranged at least partially within the housing (252) and being configured for locking the capillary (202) to the fitting (200).

39 Claims, 2 Drawing Sheets

(51) Int. Cl.
*F16L 15/08* (2006.01)
*F16L 19/02* (2006.01)
*G01N 30/02* (2006.01)

(56) References Cited

U.S. PATENT DOCUMENTS

| | | | |
|---|---|---|---|
| 5,595,406 A * | 1/1997 | Warchol | F16L 39/00 285/319 |
| 6,193,286 B1 | 2/2001 | Jones et al. | |
| 6,494,500 B1 | 12/2002 | Todosiev et al. | |
| 2004/0050866 A1 * | 3/2004 | Ingenhoven | B01L 3/0241 222/135 |
| 2006/0113794 A1 * | 6/2006 | Plant | G01N 30/6004 285/339 |
| 2006/0266719 A1 * | 11/2006 | Knight | B01L 9/06 211/74 |
| 2010/0092683 A1 * | 4/2010 | Ermantraut | G01N 35/1011 427/424 |

OTHER PUBLICATIONS

Chinese Office Action Dated Jan. 4, 2016 from related Chinese application No. 201280072435.6.

* cited by examiner

FITTING FOR ELASTICALLY-BIASING A CAPILLARY FOR A FLUID-TIGHT CONNECTION TO A FLUIDIC CONDUIT

The present application is a National Stage Application under 35 U.S.C. §371 and claims priority under 35 U.S.C. §121 from international Patent Application No. PCT/IB2012/056463 filed on Nov. 15, 2012. The entire disclosure of International Patent Application No. PCT/IB2012/056463 is specifically incorporated herein by reference.

BACKGROUND ART

The present invention relates to fluidically coupling fluidic components, in particular in a high performance liquid chromatography application.

In liquid chromatography, a fluidic sample (mobile phase) may be pumped through conduits and a column comprising a material (stationary phase) which is capable of separating different components of the fluidic analyte. Such a material, so-called beads which may comprise silica gel, may be filled into a column tube which may be connected to other elements (like a sampling unit, a flow cell, containers including sample and/or buffers) by conduits.

The flow path of the mobile phase typically comprises plural individual components coupled together, which, in turn, might also be comprised of individual sub-components. Due to the high pressure applied in most HPLC applications, pressure sealing of the components in and along the flow path is required. Sealings should also provide for a small dead volume and low carryover.

A so called fitting is a fluidic component being capable of providing a sealed connection between a capillary and another fluidic conduit (such as another capillary or a channel in a substrate or the like).

U.S. Pat. No. 4,991,883 discloses an apparatus for connecting first and second conduits having first and second bores, respectively, to provide communication between the first and second bores. The apparatus includes a base attached to the first conduit and a cap attached to the base. A follower is slidably disposed in the cap and is provided with a passageway, the second conduit extending through the passageway. A ferrule is received on the second conduit, the ferrule having a first end and a second end. The follower is biased against the first end of the ferrule. The first bore in the first conduit has a frustoconical surface which defines a receiving formation for the ferrule, the ferrule having a portion which is circular when viewed in transverse cross section. When the second end of the ferrule is urged in the receiving formation by the action of the biasing spring, the ferrule engages the frustoconical surface defining the receiving formation in substantially line contact.

U.S. Pat. No. 5,234,235 discloses an apparatus for connecting first and second conduits, which may be capillary columns, having first and second bores, respectively, to provide communication between the first and second bores for high temperature operation over wide variations in temperature. A monolithic fused quartz seating element is removably insertable into a seating chamber of a base that may be comprised of steel or other metal. The monolithic fused quartz seating element may be cylindrical and have frustoconical surfaces defining first and second receiving formations. First and second slidable followers biased by first and second quartz springs apply pressure against first and second ferrules to seal between the first and second receiving formations, and the first and second conduits, respectively.

U.S. Pat. No. 6,193,286 discloses a fitting which provides a means of making a union between a tube and a female fitting with low dead volume and without the use of tools. The fitting is comprised of a tube member that is pressed into the female fitting to automatically remove dead volume. The tube member is pressed into the fitting by a spring with the appropriate tension to hold the tube member against the expected pressure. The fitting also is comprised of a two piece nut assembly. The forward nut compresses a ferrule to create the high-pressure seal. The rearward nut is attached to the forward nut and provides compression and a holding means for the spring.

U.S. Pat. No. 6,494,500 discloses a universal self-adjusting high pressure liquid connector for use with high pressure liquid chromatography (HPLC) columns requiring liquid-tight and leak-free seals between fittings and unions. The apparatus provides a liquid-tight seal between the end of a HPLC end fitting and an end cap thereby eliminating any potential dead volume in the area of the connection. The apparatus comprises a body, a fixed ferrule, a replaceable ferrule, a stem disposed in the body and a biasing spring slidingly mounted on a capillary tube that extends through the connector. The spring biases the capillary tube of the connector into the HPLC end fitting, self-adjusting and maintaining a pressure sufficient to ensure a liquid-tight seal notwithstanding the depth of the HPLC tube stop or ferrule stop of the mating HPLC column.

However, the requirements regarding sealing performance and mechanical stability of a fluidic component of fluidic measurement devices increases with further increasing operation pressure values. At the same time, fast and easy handling of such a fitting by a user is required.

DISCLOSURE

It is an object of the invention to provide an efficiently sealing fluidic component for a fluidic device which is simple in operation.

According to an exemplary embodiment of the present invention, a fitting for providing a fluid connection between a capillary and a fluidic conduit of a fluidic component is provided, the fitting comprising a male piece and a female piece for connection with the male piece, wherein the male piece comprises a housing with a capillary reception configured for receiving the capillary, wherein a part of the capillary being received in the capillary reception is circumferentially covered by a sleeve (particularly only a part of the capillary portion being received in the capillary reception is circumferentially covered by the sleeve, wherein a remaining part of the capillary portion being received in the capillary reception can be free of the sleeve), an elastic biasing mechanism being arranged at least partially within the housing, being configured for biasing the capillary against the female piece and being supported (particularly directly, i.e. without an intermediate member in between, or indirectly, i.e. via an intermediate member such as a clamping ring in between) by (or against) the sleeve, and a locking mechanism (for instance a latch or snap fit mechanism) being arranged at least partially within the housing and being configured for locking the capillary to the fitting (for instance providing a form fit and/or a friction fit; the capillary may be locked directly to the locking mechanism itself).

According to another exemplary embodiment, a fluidic device for conducting a fluidic sample is provided, wherein the fluidic device comprises a fluidic component having a fluidic conduit, a capillary, and a fitting having the above mentioned features for providing a fluid connection between the capillary when received in the fitting and the fluidic conduit of the fluidic component when connected to or forming part of the fitting for conducting the fluidic sample through the fluidic device.

According to still another exemplary embodiment, a method for providing a fluid connection between a capillary and a fluidic conduit of a fluidic component by a fitting comprising a male piece and a female piece is provided, wherein the method comprises receiving the capillary in a capillary reception within a housing of the male piece, wherein a part of the capillary received in the capillary reception is circumferentially covered by a sleeve, locking the capillary to the fitting by a locking mechanism, being arranged at least partially within the housing, of the male piece, and connecting the male piece with the female piece to thereby form a fluid-tight connection between the capillary and the fluidic conduit forming part of or being in fluid connection with the female piece, wherein the capillary is elastically biased against the female piece by an elastic biasing mechanism of the male piece supported by the sleeve, the elastic biasing mechanism being arranged at least partially within the housing.

In the context of the present application, the term "elastic biasing mechanism" may particularly denote a mechanism which provides a forwardly directed biasing force and has an elastic behavior. Elasticity is a physical property of materials or members which return to their original shape or configuration after the stress or force that caused their deformation is no longer applied. Such a deformation may be an intrinsic deformation of the elastic biasing mechanism, such as the compression of a helical spring causing the helical spring to tend to return to its force-free state (in this example, energy is stored within the elastic biasing mechanism during the deformation). However, such a deformation may also be a relative motion between individual bodies of the elastic biasing mechanism, such as the relative motion between two magnetic elements causing the magnetic elements to tend to return to a state with a weaker repellant force or a higher attracting force between the magnetic elements (in this example, energy is stored in a magnetic field generated by the magnetic elements of the elastic biasing mechanism during the deformation).

In the context of the present application, the term "front" may particularly denote a portion of the fitting with an orientation towards the female piece and the fluidic conduit. Correspondingly, the term "back" may particularly denote a portion of the fitting with an orientation towards the male piece and the capillary reception.

According to an exemplary embodiment, a fitting for forming a fluid-tight coupling between a lumen of a capillary and a connected fluidic conduit (such as the lumen of another capillary or a channel in a solid body) is provided which benefits from both a high sealing force as well as a small dead volume at a connection between male piece and female piece. In fluidic systems for high pressure applications, particularly liquid chromatography apparatuses, a fluidic sealing at a connection between a lumen of a capillary and a connected fluidic conduit can be formed by a pressing force of a ferrule or the like against an inner wall of the female piece to be connected with the male piece having the ferrule. The capillary may extend beyond a front end of the ferrule so as to abut against the fluidic conduit. According to an embodiment of the invention, a spring or the like elastically biases such a standard capillary forwardly against a delimiting wall of the female piece. Such a standard capillary can be a tubular capillary being circumferentially surrounded only along a section thereof by a sleeve or socket which may be fixedly connected to the capillary. It is advantageous that embodiments of the invention may use such a standard capillary. The spring-like elastically biasing mechanism may push a rear flange ring of such a sleeve forwardly which will, in turn, result in a forward biasing of the capillary against the fluidic conduit of or fluidically coupled to the female piece. The possibility to use a standard capillary while providing such a forward biasing of the capillary against the connection piece keeps the dead volume at the front end of the capillary small and simplifies manual handling of the capillary in the fitting, since the fitting itself will bias the capillary forwardly. Additionally, the locking of the capillary to the fitting ensures that a user only needs to guide the capillary from a rear or backward position into the male piece of the fitting until the locking occurs, which may provide the user with a haptic feedback that the capillary is now properly mounted. Applying an automatic pre-load to the capillary also allows for an automatic adjustment to different port depths. Further, there is no need to push the capillary manually during fastening the fitting to avoid dead volumes, resulting in a user convenient handling and failure robust operation.

In the following, further embodiments of the fitting, the fluidic device and the method will be explained.

In an embodiment, the elastic biasing mechanism is supported by an annular flange face of the sleeve. Therefore, the border between the socket-surrounded portion of the capillary and a socket-free portion of the capillary may be used as a grip surface for supporting the biasing mechanism. Therefore, a pressing force can be applied from the biasing mechanism to the annular flange face of the sleeve or socket.

In an embodiment, the locking mechanism is configured for locking the capillary at an annular flange face of the sleeve. Thus, the annular flange face of the sleeve may not only serve as a support surface for the elastic biasing mechanism but may also define a step and hence the position at which the locking occurs. The mechanical discontinuity at the position of the annular flange face may hence be synergistically used as a locking element.

In an embodiment, the elastic biasing mechanism is supported (or mounted or assembled) so as to press the sleeve forwardly towards the female piece (in an operation state in which the female piece and the male piece are interconnected). By taking this measure, the dead volume is reduced and the fitting becomes particularly suitable for high pressure application.

In an embodiment, the elastic biasing mechanism is supported between the sleeve (at one end of the elastic biasing mechanism) and an abutment face at a back side of the housing (at the opposing end of the elastic biasing mechanism). Therefore, in this embodiment the other end of the elastic biasing mechanism is supported by an inner wall of the male piece which delimits the capillary reception.

In an embodiment, the elastic biasing mechanism comprises a spring. In this context, a spring is considered as a mechanical component which can be compressed upon applying a force and which goes back to an equilibrium state if the force is released. Such a mechanical component may also be expandable upon applying a force and goes back to the equilibrium state if the force is released. Hence, such a spring generates a biasing force when being compressed and/or expanded.

In an embodiment, the spring comprises a mechanical spring, for instance a helical spring, a disc spring or a leaf spring. However, other kinds of mechanical springs are possible. Such a mechanical spring is a cost-efficient member which can press the capillary reliably and over a long time period forwardly without suffering from aging effect or the like.

In another embodiment, the spring comprises a magnetic spring. In the context of this application, the term "magnetic spring" is used for an arrangement of two or more magnetic elements which are mounted in such a manner so as to mutually exert an attracting or a repellent force with an amplitude being dependent on the mutual distance between the magnetic elements. Since the reduction of a distance between two repellent magnetic elements (which is analogue to the compression of a mechanical spring) or the increase of a distance between two attracting magnetic elements (which is analogue to the expansion of a mechanical spring) results in a restoring magnetic force, also a plurality of magnetic elements may be capable of providing an elastic biasing effect.

In an embodiment, the magnetic spring comprises a first magnetic element and a second magnetic element configured to attract or to repel one another and being mounted movably relative to one another. For instance, one of the magnetic elements may be mounted fixedly and the other one may be mounted movably within the capillary reception. It is also possible that both magnetic elements are mounted movably within the capillary reception when the magnetic elements are repellant. The magnetic elements may be permanent magnets.

In an embodiment, the first magnetic element is mounted at a fixed position within the housing of the male piece, and the second magnetic element is mounted movably within the housing so as to apply a biasing force to the sleeve. By taking this measure, the number of movable elements may be kept very small and the elastic biasing effect may be nevertheless achieved.

In an embodiment, the elastic biasing mechanism comprises a fluid-based spring, such as a hydraulic spring or a pneumatic spring (like a gas pressure spring). In this context, the term fluid denotes a gas or a liquid. If a gas accommodated within a flexible surrounding wall is compressed by reducing the volume of the flexible wall, the gas has the tendency of expanding, thereby applying an elastic biasing force. In view of the smaller compressibility of liquids, this effect can be made even stronger with liquids.

In an embodiment, the male piece comprises a clamping ring being axially interposed between the elastic biasing mechanism and the sleeve and being shaped so as to convert an axial biasing force exerted by the elastic biasing mechanism into an at least partially radial gripping force exerted to the capillary surrounded by the sleeve. For example, such a clamping ring may have a slanted surface which can serve as a force direction converter. By applying an axial force to such a clamping ring, it may convert it, inter alia, into a component thereof being capable of operating radially inwardly, so as to achieve a gripping effect between capillary and clamping ring.

In an embodiment, the elastic biasing mechanism comprises a first magnetic element fixed to the housing and a second magnetic element mounted movable in the capillary reception and attracting the first magnetic element, wherein the male piece comprises a clamping ring being axially interposed between the second magnetic element on the one hand and the first magnetic element and the sleeve on the other hand and being shaped so as to convert an axial biasing force exerted by the attracting magnetic elements into an at least partially radial gripping force exerted to the capillary surrounded by the sleeve. Since two attracting magnetic elements have the tendency of reducing the distance between them, they may exert a magnetic biasing force when being separated from one another. With the help of a clamping ring having a correspondingly slanted surface, the attracting magnetic force exerted in an axial direction may be at least partially converted into a radial force.

In an embodiment, the clamping ring has a tapering back part and a widening front part, the tapering back part serving for centering the capillary along the capillary reception upon insertion from the back of the male part, and the widening front part serving for locking the capillary to the fitting upon forwarding the capillary to such an extent that a back end of the sleeve is transferred from the tapering front part into the widening back part. Thus, when a user guides the capillary with the socket or sleeve along the capillary reception, a capillary may first be centered by the tapering back part before being locked to the fitting when advancing beyond the transition portion between the tapering back part and the widening front part.

In an embodiment, the elastic biasing mechanism comprises a first magnetic element mounted movable or fixed to the housing and a second magnetic element mounted movable in the capillary reception and repelling the first magnetic element. The male piece may further comprise a clamping ring being attached to a front flange face of the second magnetic element opposing a back surface of the second magnetic element facing the first magnetic element, wherein the clamping ring is lockable to the sleeve. Two repelling magnetic elements may exert an elastic biasing force. In combination with the clamping ring, these components may function as elastic biasing mechanism and locking mechanism at the same time.

In an embodiment, the clamping ring has a support annulus and a plurality of beams (for instance four beams) protruding inwardly from the support annulus for being bent upon interaction with the sleeve. The beams may be elongated axially by the sleeve for providing a locking force. In a force-free state they may be arranged coplanar with one another and with the support annulus.

In an embodiment, the elastic biasing mechanism and the locking mechanism are integrally formed as a single component, particularly as an injection molded component. Thus, the system can be manufactured with low costs.

In an embodiment, the single component has an axial lumen for receiving the capillary, an axial slit and multiple radial slits for providing a spring property, an annular front flange for abutting against an annular back flange of the sleeve, and an annular protrusion for locking at an annular recess of the housing. Such a member has sophisticated properties and may nevertheless be manufactured with low costs as an injection molded component.

In an embodiment, the male piece comprises an annular cap inserted into a back portion of the capillary reception of the housing and being configured for preventing the elastic biasing mechanism from leaving the capillary reception, particularly engaging a back end of the elastic biasing mechanism. Such an annular cap may prevent undesired loss of the capillary and other components after insertion into the housing.

In an embodiment, the capillary reception has a neck in a central portion of the housing, the neck connecting a wider back portion with a wider front portion of the capillary reception. In an embodiment, the wider back portion accommodates at least part of the elastic biasing mechanism and at least part of the locking mechanism. In a further embodiment, the male piece comprises a clamping chuck accommodated in the wider front portion, and a ferrule abutting against the clamping chuck, being accommodated partially in and protruding over the wider front portion and being configured for sealingly abutting against a sealing surface of the female piece upon connecting the male piece and the female piece. Therefore, the narrow neck may be sandwiched between two wider sections of a basically bar-bell shaped capillary reception. The wider back portion may house the elastic biasing mechanism and the locking mechanism, whereas the wider front portion may house ferrule and ferrule chuck for providing actual sealing performance with the female piece.

In an embodiment, the ferrule has a tubular back part accommodated in the wider front portion and has a tapering front part protruding over the wider front portion. The ferrule hence has some arrow-like shape and can be pressed forwardly by the elastic biasing mechanism as well as the clamping chuck.

In an embodiment, the male piece comprises a first connection element, particularly an external thread, and the female piece comprises a second connection element, particularly an internal thread, being configured correspondingly to the first connection element so that the first connection element and the second connection element are connectable to form a connection, particularly a screwing connection, between the male piece and the female piece. Although a screwing connection between male piece and female piece may be preferred, it is also possible to connect them by another connection means, such as a snap lock or a bayonet connection.

In an embodiment, the locking mechanism is configured so that the locking of the capillary to the fitting is releasable by applying a locking release force for removing the capillary from the capillary reception via a back side of the male piece. Therefore, a user may pull out the capillary (opposite to the insertion direction thereof) with a force exceeding a certain threshold value to overcome the locking force of the locking mechanism. Thus, both assembly and disassembly of the capillary is very simple in terms of handling and can be done without tools.

In an embodiment, the method comprises inserting the capillary in the capillary reception from a back side of the male piece by a user applying a locking force until the capillary is locked to the fitting. Therefore, a very simple system is provided which can be operated even by a less skilled user. The user simply uses a standard capillary consisting of a tubular core element surrounded section-wise by the socket and inserts the capillary from a rear position into the capillary reception of the male part. Since the locking force has to be exceeded for locking the capillary to the fitting, the user will receive a haptic feedback when the locking has occurred.

In an embodiment, the method comprises removing the capillary from the capillary reception via a back side of the male piece by a user overcoming a locking release force with which the capillary is locked to the fitting. In an embodiment, the locking release force is higher than the locking force. The system can also be disassembled by simply pulling the capillary outside of the fitting. However, in order to prevent undesired removal of the capillary from the fitting, the locking release force which has to be exceeded by a user for removal the capillary from the fitting is larger than the locking force. Therefore, the user again gets a haptic feedback upon removing the capillary from the fitting, and at the same time the higher locking release force functions as a safety or warning feature.

Fluidic devices according to exemplary embodiments may be particularly suitable for use as fluidic connection pieces for connecting parts of a fluidic instrument such as a liquid chromatographic system or the like. For example, columns, fractioners, detectors, or the like, of a liquid chromatography apparatus may be connected as fluidic components of such a fluidic device.

In an embodiment, at least the part of the capillary being received in the capillary reception is at least partially circumferentially covered by a sleeve. Such a tubular sleeve may locally thicken the capillary and may be made of a metallic structure which is pressed circumferentially onto the capillary, for instance by crimping, so that it covers the entire perimeter of the capillary.

In an embodiment, the fluidic component is a processing element configured for processing the fluidic sample. Thus, such a processing element may process the fluid, for instance separate it, purify it, apply a tempering step, or the like.

Particularly, the processing element may be a chromatographic separation column which may separate different fractions of a fluidic sample due to a different affinity of the various fluidic fractions to a stationary phase of the separation column. For instance, by applying a gradient run, the trapped fractions may be released from the separation column individually, thereby separating them.

The fluidic device may comprise a processing element filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluoroethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The fluidic device may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid Chromatography (HPLC) by which different fractions of an analyte may be separated, examined and analyzed.

The fluidic device may be configured to conduct the mobile phase through the system with a high pressure, particularly of at least 600 bar, more particularly of at least 1200 bar (for instance up to 2000 bar).

The fluidic device may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less (for instance down to 15 µm or 12 µm). The analysis system may also be configured as a nanofluidic device. The term "nanofluidic device" may particularly denote a fluidic device as described herein which allows to convey fluid through nanochannels with a flow rate of less than 100 nl/min, particularly of less than 10 nl/min.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
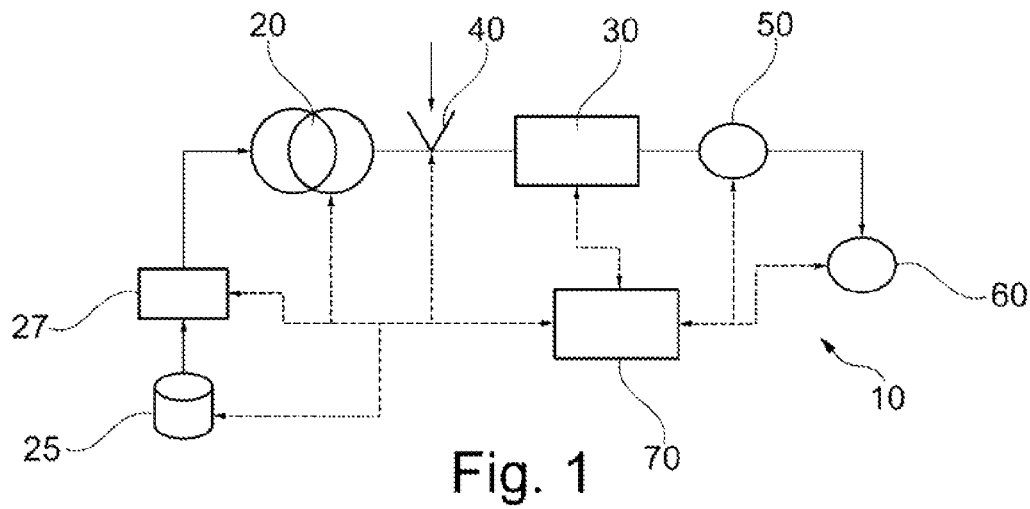
FIG. 1 shows a liquid separation device in accordance with embodiments of the present invention, particularly used in high performance liquid chromatography (HPLC).

The illustrations in the drawings are schematic.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure und downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.) The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

From the example of FIG. 1, it can be seen that the flow path of the mobile phase typically comprises plural individual components, such as pump 20, separating device 30, sampling unit 40, and detector 50, which are coupled together and which might also be comprised of individual sub-components. Also, fluid conduits, e.g. capillaries, for conducting the fluid are provided as indicated by the solid connections in FIG. 1. Coupling of parts, components and fluid conduits, in particular when using exchangeable or modular parts, is usually provided by using fittings.

For transporting liquid within the liquid separation system 10, typically tubings (e.g. tubular capillaries) are used as conduits for conducting the liquid. Fittings are commonly used to couple plural tubings with each other or for coupling a fluid conduit (e.g. a tubing) to any device. For example, fittings can be used to connect respective fluid conduits to an inlet and an outlet of the chromatographic column 30 in a liquid-sealed fashion. Any of the components in the fluid path (solid line) in FIG. 1 may be connected by fluid conduits e.g. using fittings. While the fluid path after the column 30 is usually at lower pressure, e.g. 50 bar or below, the fluid path from the pump 20 to the inlet of the column 30 is under high pressure, currently up to 1200 bar, thus posing high requirements to fluid tight connections. Due to the high pressure applied in most HPLC applications, pressure sealing of the components in and along the flow path is required.

The various exemplary embodiments of spring biased fittings described in the following overcome the conventional need to push a capillary manually during fastening the fitting to avoid dead volumes. With the described embodiments, a need for a third hand of a user is dispensable, and the fitting is more error-robust. Such embodiments may provide for an automatic pre-load and automatic adjustment to different port depths.

In the following, referring to FIG. 2, a fitting 200 for providing a fluid connection between a capillary 202 and a fluidic conduit 204 according to an exemplary embodiment of the invention will be explained. The fluidic conduit 204 may form part of a fluidic component such as chromatographic column 30, not shown in FIG. 2. The fluidic conduit 204 may alternatively be in fluid communication with a separate, connectable fluidic component, not shown in FIG. 2. The fitting 200 comprises a male piece 240 and a correspondingly shaped and configured female piece 250 for connection with the male piece 240.

The male piece 240 comprises a housing 252 with an internal recess serving as capillary reception 212, hence being configured for receiving the capillary 202. As can be taken from FIG. 2, a part of the capillary 202 portion being received in the capillary reception 212 is circumferentially covered by a fixedly fastened socket or sleeve 214 which cannot be removed from the capillary 202. The remainder of the capillary 202 is free of such a sleeve 214 so that a step is formed at a rear flange face of the sleeve 214. The capillary 202 and the sleeve 214 may both be formed of a metallic material such as stainless steel. The capillary 202 can be embodied as a flexible capillary.

A helical spring 206 is located within the capillary reception 212 in housing 252 and is mounted in such a way that it biases the capillary 202 forwardly against the female piece 250. At a front end thereof, the helical spring 206 is supported by the sleeve 214 via a clamping ring 208 in between. More precisely, the front end of the helical spring 206 is supported, indirectly via the clamping ring 208, by a rear annular flange face 254 of the sleeve 214 functioning as a support structure. The helical spring 206 is supported within the housing 252 so as to press the sleeve 214 forwardly towards the female piece 250. As can furthermore be taken from FIG. 2, the back end of the helical spring 206 abuts against an abutment face 256 at the back side of the housing 252, more precisely at a step of an annular cap 260 closing a rear opening of the housing 252, whereas the front end of the helical spring 206 is supported against the sleeve 214. The helical spring 206 is thereby retained with a pre-compression between the annular flange face 254 of the sleeve 214 and the abutment face 256 at the back side of the housing 252. The annular cap 260 is inserted into a back portion of the capillary reception 212 of the housing 252 for preventing the helical spring 206 from leaving the capillary reception 212. The annular cap 260 engages a back end of the helical spring 206. Therefore, it can be reliably ensured that the helical spring 206 is not lost and does not leave the male piece 240. The cap 260 serves as a capsule for holding the helical spring 206 so that the helical spring 206 cannot be lost.

Figure 2:
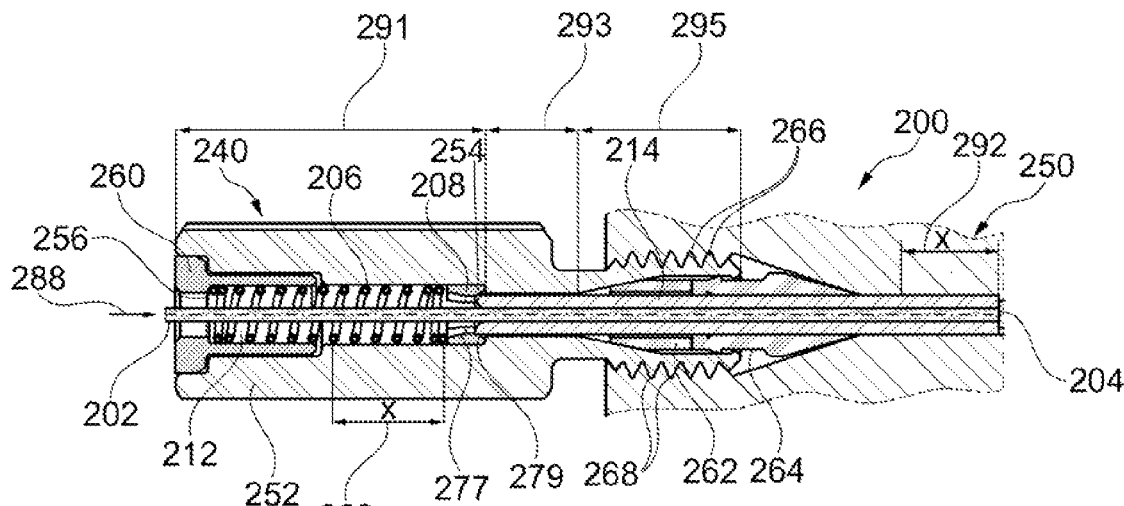
FIG. 2 illustrates a fitting for providing a fluid connection between a capillary and a fluidic conduit according to an exemplary embodiment of the invention, wherein a capillary is pushed into the fitting by a helical spring and a clamping ring is used.

As can furthermore be taken from FIG. 2, the clamping ring 208 arranged within the housing 252 serves as a locking mechanism for locking the capillary 202 to the fitting 200. This locking prevents the capillary 202 from being unintentionally pushed out of a back end of the capillary reception 212. The damping ring 208 is configured for locking the capillary 202 at the annular flange face 254 of the sleeve 214. The male piece's 240 clamping ring 208 is axially interposed between the elastic helical spring 206 and the sleeve 214 and is shaped so as to convert an axial biasing force exerted by the helical spring 206 into a partially radial gripping force exerted to the capillary 202 surrounded by the sleeve 214. This is achieved by a slanted surface of the clamping ring 208.

Moreover, the clamping ring 208 has, in a view along insertion direction 288, a tapering back part 277 and a widening front part 279. The tapering back part 277 radially centers the capillary 202 in the capillary reception 202 upon inserting it from the back of a male part 240 along the insertion direction 288. The widening front part 279 locks the capillary 202 to the fitting 200 upon forwarding the capillary 202, along insertion direction 288, to such an extent that a back end of the sleeve 214 passes from the tapering back part 277 into the widening front part 279.

For operating the fitting 200 shown in FIG. 2, a user slides the capillary 202 covered by the socket or sleeve 214 along insertion direction 288 into the capillary reception 212. At a certain position during this pushing motion, socket or sleeve 214 passes into the widening front part 279, thereby locking the clamping ring 208 to the sleeve 214 around the capillary 202. The helical spring 206 serves to preload the capillary 202 into the port. A suspension travel x is denoted with reference numeral 290. It corresponds to a distance x denoted with reference numeral 292 at a front side of the fitting 200.

FIG. 2 furthermore shows that the capillary reception 212 has a neck 293 in a central portion of the housing 252, wherein the neck 293 connects a wider back portion 291 of the capillary reception 212 and a wider front portion 295 of the capillary reception 212. The wider back portion 291 accommodates the helical spring 206 and the clamping ring 208. In contrast to this, the wider front portion 295 accommodates a clamping chuck 262 and a part of a ferrule 264. The ferrule 264 abuts against the clamping chuck 262 at a back portion of the ferrule 264. The ferrule 264 is accommodated partly in and protrudes partially beyond the wider front portion 295. The ferrule 264 is configured for sealingly abutting against the sealing surface of the female piece 250 upon connecting the male piece 240 and the female piece 250. The ferrule 264 has a tubular back part accommodated partly in the wider front portion 295 and has a tapering front part protruding over the wider front portion 295. Hence, the ferrule 264 which may be made of a mechanically stable plastic material such as PEEK has an arrow-like shape and contributes to the sealing between the male piece 240 and the female piece 250.

As can furthermore be taken from FIG. 2, the male piece 240 has an external thread 266 as a first connection element. The female piece 250 has a cooperating second connection element which is embodied as an internal thread 268. The internal thread 268 and the external thread 266 cooperate to be connectable to one another by screwing to thereby form a screw connection between the male piece 240 and the female piece 250, simultaneously forming a sealed connection between capillary 202 and fluidic conduit 204. In view of the biasing force of the helical spring 206, the capillary 202, upon forming the screwing connection, abuts tightly against the fluidic conduit 204 of the female piece 250 with small dead volume. Forming the screwing connection will also result in a forward biasing of the ferrule 264 against an inner wall of the female piece 250, thereby providing for a fluid-tight and high pressure resistant connection here having only a very small dead volume.

Summarizing, in the exemplary embodiment shown in FIG. 2, the capillary 202 is pushed into the fitting 200. The clamping ring 208, which is connected to the spring 206, holds the capillary 202 and makes it possible to preload the capillary 202. This clamping ring 208 is radially movable so that the capillary 202 can also be removed without any tools. This embodiment supports standard capillaries 202 with a standard socket or sleeve 214.

In the following, referring to FIG. 3, a fitting 200 according to another exemplary embodiment of the invention will be explained.

Figure 3:
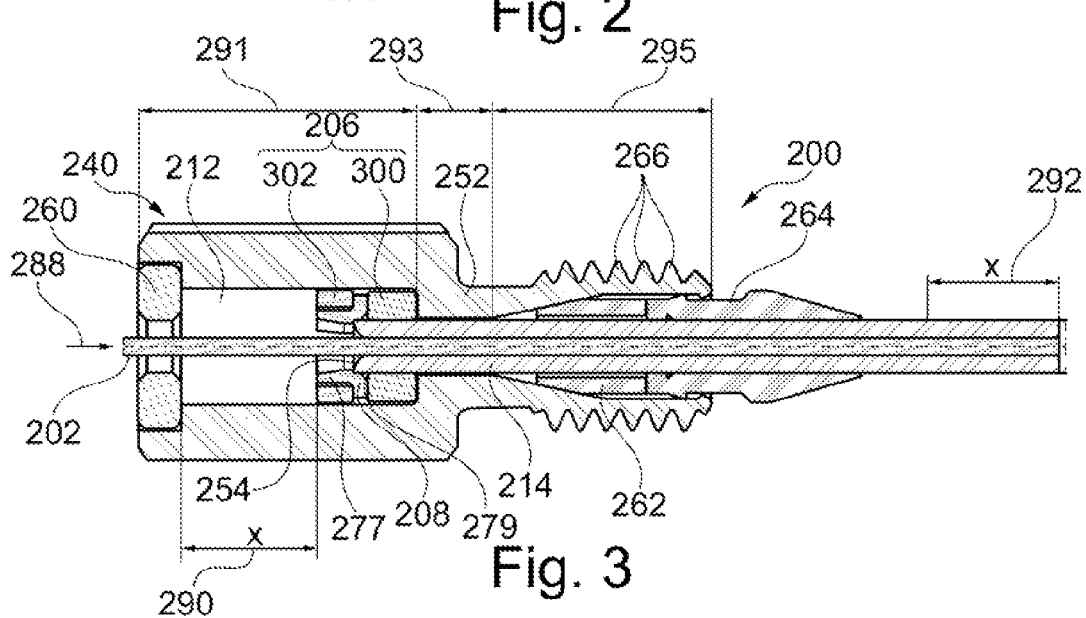
FIG. 3 illustrates a fitting for providing a fluid connection between a capillary and a fluidic conduit according to another exemplary embodiment of the invention, wherein a capillary is pushed into the fitting by a magnetic force and a clamping ring is used.

In the embodiment of FIG. 3, an elastic biasing mechanism is formed by an annular first magnetic element 300 mounted at a fixed position within the housing 252 at the male piece 240, and a cooperating annular second magnetic element 302 which attracts the first magnetic element 300 and which is mounted movably within the housing 252 so as to apply a biasing force to the sleeve 214. The male piece 240 again comprises a clamping ring 208 which is actually interposed between the second magnetic element 302 on the one hand and the first magnetic element 300 and the sleeve 214 on the other hand. The clamping ring 208 is furthermore shaped with a slanted front surface so as to convert an axially directed biasing force exerted by the attracting magnetic elements 300, 302 into a partially radial gripping force which is exerted to the capillary 202 surrounded by the sleeve 214. The first magnetic element 300 is pressed into the male piece 240, i.e. is connected by a press-fit connection to housing 252. In contrast to this, the second magnetic element 302 is actually movable in the counterbore. The clamping ring 208 again serves to grip the capillary 202.

In the embodiment shown in FIG. 3, the capillary 202 is also pushed forwardly within the fitting 200 by the clamping ring 208 connected to the magnetic spring 206.

Figure 4:
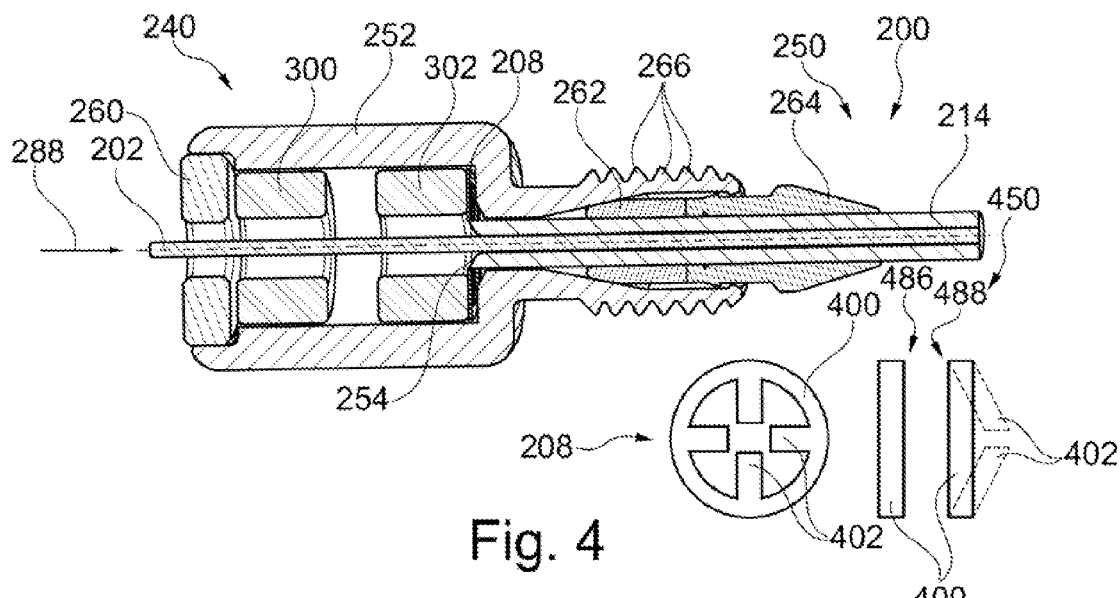
FIG. 4 and FIG. 5 illustrate two different operation modes of a fitting for providing a fluid connection between a capillary and a fluidic conduit according to still another exemplary embodiment of the invention, wherein two magnets are used cooperating as a magnetic spring.
Figure 5:
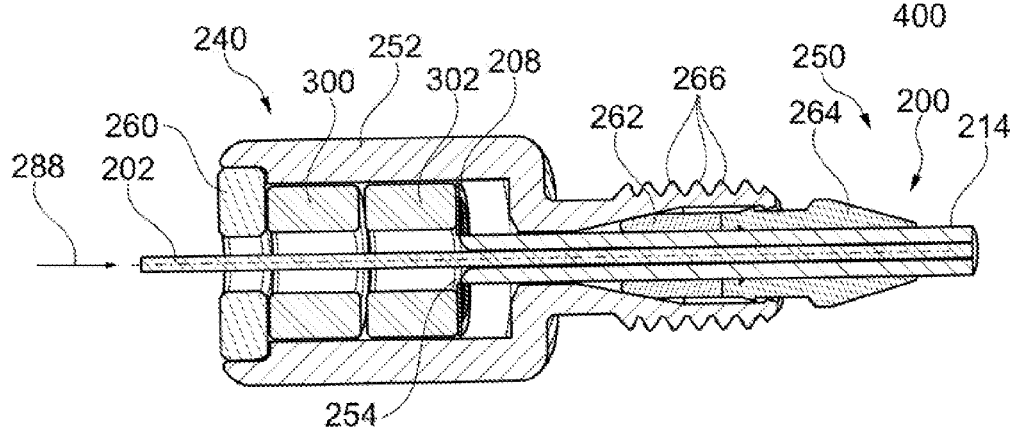

FIG. 4 and FIG. 5 show a fitting 200 according to yet another exemplary embodiment in two operation modes. In the embodiment of FIG. 4 and FIG. 5, an annular first magnetic element 300 is mounted fixed to the housing 252. An annular second magnetic element 302 is mounted movable within the capillary reception 212 and repels the first magnetic element 300. Also in this embodiment, the male piece 240 comprises a clamping ring 208 which is attached to a front flange face of the second magnetic element 302 opposing a back surface of the second magnetic element 302 facing the first magnetic element 300. The damping ring 208 is lockable to the sleeve 214.

A detail 450 in FIG. 4 shows how such a clamping ring 208 may be configured. In the shown embodiment, the clamping ring 208 has a support annulus 400 and four beams 402 arranged in a cross pattern and protruding inwardly from the support annulus 400 for being bent upon interaction with the sleeve 214. FIG. 4 shows a plan view of the clamping ring 208 as well as a first side view 486 in a force-free state and a second side view 488 in a state in which the beams 402 are elongated axially as a consequence of a locking force.

In the embodiment shown in FIG. 4 and FIG. 5, two magnets 300, 302 are used instead of a mechanical spring. One of the magnets 300 is pressed into the male fitting nut and the other magnet 302 is axially movable. The capillary 202 is held by the clamping ring 208, which is positioned adjacent to one of the two magnets 300, 302. Because of the magnetic force, the capillary 202 can be preloaded. Also here the capillary 202 can be removed by pulling it out.

Figure 6:
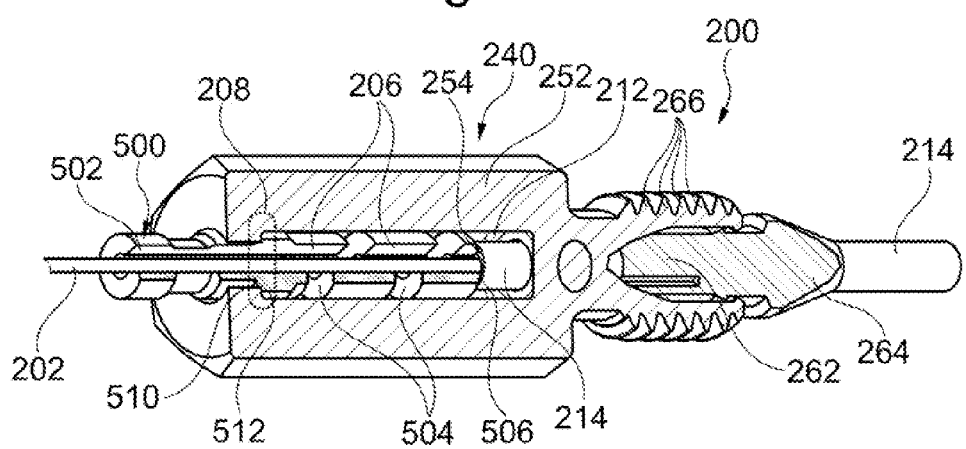
FIG. 6 illustrates a fitting for providing a fluid connection between a capillary and a fluidic conduit according to yet another exemplary embodiment of the invention, wherein a molded plastic part pre-loads the capillary.

In the embodiment of FIG. 6, a fitting 200 according to still another exemplary embodiment is shown in which the elastic biasing mechanism and the locking mechanism are integrally formed as a single component 500 which is embodied as an injection molded component. The single component 500 has an axial lumen for receiving the capillary 202, has an axial slit 502, has multiple radial slits 504 for providing a spring property, has an annular front flange 506 for abutting against an annular back flange 254 of the sleeve 214, and has an annular protrusion 510 for locking at an annular recess 512 at the rear end of the capillary reception 212 of the housing 252.

In the embodiment shown in FIG. 6, a molded plastic part with special features, i.e. the single component 500, preloads the capillary 202. This part has the functions to connect the capillary 202 removable with fitting 200 and includes a spring-like body to preload the capillary 202. With a clip-function the single component 500 can be clipped on and off to a standard flexible capillary 202 with socket or sleeve 214. The integrally formed component 500 may also be denoted as a molded spring snap-click connector. At a position 208, it may be locked to the fitting 200.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fitting for providing a fluid connection between a capillary and a fluidic conduit of a fluidic component, the fitting comprising:
   a capillary;
   a sleeve fixedly fastened to the capillary and comprising an annular flange face surrounding the capillary; and
   a male piece configured for connection with a female piece, the male piece comprising:
   a housing with a capillary reception configured for receiving the capillary, wherein a part of the capillary being received in the capillary reception is circumferentially covered by the sleeve, and the annular flange face faces the capillary reception;
   an elastic biasing mechanism being arranged at least partially within the housing, being configured for biasing the capillary against the female piece and being supported by the sleeve; and a locking mechanism being arranged at least partially within the housing and being configured for locking the capillary to the fitting at the annular flange face.

2. The fitting according to claim 1, wherein the elastic biasing mechanism is supported by the annular flange face of the sleeve.

3. The fitting according to claim 1, wherein the elastic biasing mechanism is mounted so as to press the sleeve forwardly towards the female piece.

4. The fitting according to claim 1, wherein the elastic biasing mechanism is supported between the sleeve and an abutment face at a back side of the housing.

5. The fitting according to claim 1, wherein the elastic biasing mechanism comprises a spring.

6. The fitting according to claim 1, wherein the elastic biasing mechanism comprises a mechanical spring.

7. The fitting according to claim 6, wherein the mechanical spring comprises one of the group consisting of a helical spring, a disc spring, and a leaf spring.

8. The fitting according to claim 1, wherein the elastic biasing mechanism comprises a magnetic spring.

9. The fitting according to claim 8, wherein the magnetic spring comprises a first magnetic element and a second magnetic element which are configured to attract or to repel one another and being mounted movably relative to one another.

10. The fitting according to claim 9, wherein the first magnetic element is mounted at a fixed position within the housing of the male piece, and the second magnetic element is mounted movably within the housing so as to apply a biasing force to the sleeve.

11. The fitting according to claim 1, wherein the elastic biasing mechanism comprises a fluid-based spring.

12. The fitting according to claim 11, wherein the fluid-based spring comprises one of the group consisting of a hydraulic spring, a pneumatic spring, and a gas pressure spring.

13. The fitting according to claim 1, wherein the male piece comprises a clamping ring being axially interposed between the elastic biasing mechanism and the sleeve and being shaped so as to convert an axial biasing force exerted by the elastic biasing mechanism partially into a radial gripping force exerted to the capillary surrounded by the sleeve.

14. The fitting according to claim 1,
wherein the elastic biasing mechanism comprises a first magnetic element fixed to the housing and a second magnetic element mounted movable in the capillary reception and attracting the first magnetic element;
wherein the male piece comprises a clamping ring being axially interposed between the second magnetic element on the one hand and the first magnetic element and the sleeve on the other hand and being shaped so as to convert an axial biasing force exerted by the attracting magnetic elements partially into a radial gripping force exerted to the capillary surrounded by the sleeve.

15. The fitting according to claim 14, wherein the clamping ring has a tapering back part and a widening front part, the tapering back part being configured for centering the capillary along the capillary reception upon insertion from the back of the male part, and the widening front part being configured for locking the capillary to the fitting upon forwarding the capillary to such an extent that a back end of the sleeve passes from the tapering front part into the widening back part.

16. The fitting according to claim 1,
wherein the elastic biasing mechanism comprises a first magnetic element mounted movable or fixed to the housing and a second magnetic element mounted movable in the capillary reception and repelling the first magnetic element;
wherein the male piece comprises a clamping ring being attached to a front flange face of the second magnetic element opposing a back surface of the second magnetic element facing the first magnetic element, the clamping ring being lockable to the sleeve.

17. The fitting according to claim 16, wherein the clamping ring has a support annulus and a plurality of beams protruding inwardly from the support annulus for being bent upon interaction with the sleeve.

18. The fitting according to claim 1, wherein the elastic biasing mechanism and the locking mechanism are integrally formed as a single component, or as a single injection molded component.

19. The fitting according to claim 18, wherein the single component or the single injection molded component comprises an axial lumen for receiving the capillary, an axial slit and multiple radial slits for providing a spring property, an annular front flange for abutting against the annular back flange, and an annular protrusion for locking to an annular recess of the housing.

20. The fitting according to claim 1, wherein the male piece comprises an annular cap inserted into a back portion of the capillary reception of the housing and being configured for at least one of:
preventing the elastic biasing mechanism from leaving the capillary reception;
engaging a back end of the elastic biasing mechanism.

21. The fitting according to claim 1, wherein the capillary reception has a neck in a central portion of the housing, the neck connecting a wider back portion and a wider front portion of the capillary reception.

22. The fitting according to claim 21, wherein the wider back portion accommodates at least part of the elastic biasing mechanism and at least part of the locking mechanism.

23. The fitting according to claim 21, wherein the male piece comprises
a clamping chuck accommodated in the wider front portion; and
a ferrule abutting against the clamping chuck, being accommodated partially in and protruding over the wider front portion and being configured for sealingly abutting against a sealing surface of the female piece upon connecting the male piece and the female piece.

24. The fitting according to claim 23, wherein the ferrule has a tubular back part accommodated in the wider front portion and has a tapering front part protruding over the wider front portion.

25. The fitting according to claim 1, wherein the male piece comprises a first connection element, and the female piece comprises a second connection element being configured correspondingly to the first connection element so that the first connection element and the second connection element are connectable to form a connection between the male piece and the female piece.

26. The fitting according to claim 1, wherein the locking mechanism is configured so that the locking of the capillary to the fitting is releasable by applying a locking release force for removing the capillary from the capillary reception via a back side of the male piece.

27. The fitting according to claim 1, wherein the locking mechanism is arranged to be axially interposed between the annular flange face and at least a portion of the elastic biasing mechanism such that the elastic biasing mechanism is supported by the sleeve via the locking mechanism.

28. A fluidic device for conducting a fluidic sample, the fluidic device comprising
a fluidic component having a fluidic conduit; and
a fitting according to claim 1 for providing a fluid connection between the capillary when received in the fitting and the fluidic conduit of the fluidic component when connected to or forming part of the fitting for conducting the fluidic sample through the fluidic device.

29. The fluidic device according to claim 28, wherein the sleeve is a tubular sleeve integrally formed with the capillary.

30. The fluidic device according to claim 28, wherein the fluidic component comprises a processing element configured for processing the fluidic sample.

31. The fluidic device according to claim 30, wherein the processing element is configured for retaining the fluidic sample being a part of a mobile phase and for allowing other components of the mobile phase to pass the processing element.

32. The fluidic device according to claim 30, wherein the processing element is a separation column.

33. The fluidic device according to claim 30, wherein the processing element comprises a chromatographic column for separating components of the fluidic sample.

34. The fluidic device according to claim 28, configured to conduct the fluidic sample through the fluidic conduit and the capillary with a high pressure.

35. The fluidic device according to claim 28, configured to conduct the fluidic sample through the fluidic conduit and the capillary with a pressure of at least 100 bar.

36. A method for providing a fluid connection between a capillary and a fluidic conduit of a fluidic component by the fitting according to claim 1, the method comprising:
receiving the capillary in the capillary reception;
locking the capillary to the fitting by the locking mechanism; and
connecting the male piece with the female piece to thereby form a fluid-tight connection between the capillary and the fluidic conduit forming part of or being in fluid connection with the female piece, wherein the capillary is elastically biased against the female piece by the elastic biasing mechanism supported by the sleeve.

37. The method according to claim 36, wherein the method comprises inserting the capillary in the capillary reception from a back side of the male piece by a user applying a locking force until the capillary is locked to the fitting.

38. The method according to claim 36, wherein the method comprises removing the capillary from the capillary reception via a back side of the male piece by a user overcoming a locking release force with which the capillary is locked to the fitting.

39. The method according to claim 37, wherein the locking release force is higher than the locking force.

* * * * *